US010636636B2

(12) United States Patent
Tautenhahn et al.

(10) Patent No.: US 10,636,636 B2
(45) Date of Patent: Apr. 28, 2020

(54) SYSTEMS AND METHODS FOR SAMPLE COMPARISON AND CLASSIFICATION

(71) Applicant: Thermo Finnigan LLC, San Jose, CA (US)

(72) Inventors: Ralf Tautenhahn, Mountain View, CA (US); Timothy J. Stratton, Sunnyvale, CA (US)

(73) Assignee: THERMO FINNIGAN LLC, San Jose, CA (US)

(*) Notice: Subject to any disclaimer, the term of this patent is extended or adjusted under 35 U.S.C. 154(b) by 353 days.

(21) Appl. No.: 15/601,487

(22) Filed: May 22, 2017

(65) Prior Publication Data
US 2017/0338089 A1 Nov. 23, 2017

Related U.S. Application Data

(60) Provisional application No. 62/340,329, filed on May 23, 2016.

(51) Int. Cl.
H01J 49/00 (2006.01)
G01N 30/72 (2006.01)
(Continued)

(52) U.S. Cl.
CPC .......... H01J 49/0036 (2013.01); G01N 30/72 (2013.01); G16C 20/70 (2019.02); G16C 20/20 (2019.02)

(58) Field of Classification Search
CPC ..... H01J 49/0036; G16C 20/70; G16C 20/20; G01N 30/72
See application file for complete search history.

(56) References Cited

U.S. PATENT DOCUMENTS 5,119,315 A * 6/1992 Kemp ................ G01N 30/8665
702/13
5,602,755 A 2/1997 Ashe et al.
(Continued)

FOREIGN PATENT DOCUMENTS

WO 02/03056 A1 1/2002
WO 2009/146345 A1 12/2009

OTHER PUBLICATIONS

Noy et al., "Robust Estimation and Graph-based Meta Clustering for LC-MS Feature Extraction", 2007 IEEE International Conference on Bioinformatics and Biomedicine, pp. 230-236.
(Continued)

Primary Examiner — Mohammad K Islam
(74) Attorney, Agent, or Firm — David A. Schell

(57) ABSTRACT

A system includes a database server and a plurality of processing nodes. The plurality of processing nodes are configured to receive mass spectrometry data from a plurality of samples; align the mass spectrometry data to correct for changes in retention time to generate a reference alignment; cluster compounds across the plurality of samples; store the reference alignment and clustered compound data to the database server; receive additional mass spectrometry data from additional samples; align the additional mass spectrometry data to a reference alignment within the database; correlate the compounds from the additional samples with the clustered compound data; classify the compounds; perform statistical analysis on the classified compounds to identify compounds meeting threshold criteria; and provide an indication of compounds meeting the threshold criteria.

20 Claims, 6 Drawing Sheets

(51) Int. Cl.
 *G16C 20/70* (2019.01)
 *G16C 20/20* (2019.01)

(56) References Cited

U.S. PATENT DOCUMENTS

| | | | | | |
|---|---|---|---|---|---|
| 5,699,269 | A | * | 12/1997 | Ashe | G01N 33/2823 436/29 |
| 5,699,270 | A | | 12/1997 | Ashe et al. | |
| 8,635,258 | B2 | * | 1/2014 | Du | G01N 30/8668 708/207 |
| 8,838,393 | B2 | * | 9/2014 | Sen Gupta | G16C 20/20 702/19 |
| 2003/0110000 | A1 | * | 6/2003 | Quimby | G01N 30/8665 702/89 |
| 2004/0113062 | A1 | * | 6/2004 | Norton | G01N 30/8624 250/282 |
| 2004/0195500 | A1 | * | 10/2004 | Sachs | H01J 49/0036 250/282 |
| 2005/0170372 | A1 | * | 8/2005 | Afeyan | C12Q 1/68 435/6.19 |
| 2005/0283316 | A1 | * | 12/2005 | Hands | G01N 33/6848 702/19 |
| 2007/0231921 | A1 | * | 10/2007 | Roder | G06K 9/6231 436/173 |
| 2010/0163721 | A1 | * | 7/2010 | Graves | G01N 33/6818 250/282 |
| 2013/0080073 | A1 | * | 3/2013 | de Corral | G01N 30/86 702/23 |
| 2014/0038217 | A1 | | 2/2014 | Gorenstein et al. | |
| 2014/0236497 | A1 | * | 8/2014 | Escher | G01N 30/8672 702/30 |
| 2014/0297201 | A1 | | 10/2014 | Knorr et al. | |
| 2014/0303903 | A1 | * | 10/2014 | Fujita | H01J 49/0036 702/23 |
| 2014/0329274 | A1 | * | 11/2014 | Bowen | G01N 33/6848 435/34 |
| 2015/0141290 | A1 | * | 5/2015 | Zhao | G01N 33/68 506/12 |
| 2015/0311052 | A1 | | 10/2015 | Geromanos et al. | |
| 2016/0141164 | A1 | * | 5/2016 | Kusch | G01N 30/8668 702/89 |
| 2018/0166265 | A1 | * | 6/2018 | Geromanos | G01N 30/72 |
| 2019/0017976 | A1 | * | 1/2019 | Nakayama | G01N 30/72 |
| 2019/0130994 | A1 | * | 5/2019 | Ruderman | G16B 20/00 |

OTHER PUBLICATIONS

Tuli et al., "Using a Spike-In Experiment to Evaluate Analysis of LC-MS Data", 2010 IEEE International Conference on Bioinformatics and Biomedicine Workshops, pp. 67-72.
Jaintly et al., "Robust Algorithm for Alignment of Liquid Chromatography-Mass Spectrometry Analyses in an Accurate Mass and Time Tag Data Analysis Pipeline", Anal. Chem. 2006, 78, pp. 7397-7409.
Tibshirani et al., "Sample classification from protein massspectrometry, by 'peak probability contrasts'", Bioinformatics, vol. 20 (17) 2004, pp. 3034-3044.
Wu et al., "Comparison of statistical methods for classification of ovarian cancer using mass spectrometry data", vol. 19 (13) 2003, pp. 1636-1643.
Xia et al., "MetaboAnalyst 3.0—making metabolomics moremeaningful", Nucleic Acids Research, 2015, vol. 43, W251-W257.
Xia et al., "MetaboAnalyst: a web server for metabolomic data analysis and interpretation", Nucleic Acids Research, 2009, vol. 37, pp. W652-W660.
Zhang et al., "Recursive SVM feature selection and sample classification for mass-spectrometry and microarray data", BMC Bioinformatics 2006, 7:197, pp. 1-13.

* cited by examiner

SYSTEMS AND METHODS FOR SAMPLE COMPARISON AND CLASSIFICATION

FIELD

The present disclosure generally relates to the field of mass spectrometry including systems and methods for sample comparison and classification.

INTRODUCTION

Mass spectrometry can be used to perform detailed analysis on samples. Furthermore, mass spectrometry can provide both qualitative (Is compound X present in the sample) and quantitative (how much of compound X is present in the sample) data for a large number of compounds in a sample. These capabilities have been used for a wide variety of analysis, such as to test for drug use, determine pesticide residues in food, monitor water quality, and the like. However, in these contexts, mass spectrometry is generally used to detect/quantify a known set of compounds.

In some fields, such as forensic drug testing or food safety, novel compounds are developed periodically that are not part of the set of known compounds. For example, a new designer drug may be developed and used on the street before validated tests for the new designer drug are added to the standard set of forensic drug tests. In another example, athletes may utilize new performance enhancing drugs before tests have been developed to detect their use. In yet another example, compounds may be used to adulterate food products that are not routinely tested for during food safety testing.

As such, there is a need for systems and methods to allow easy comparison and classification of samples to identify samples and compounds within samples that are outside of normal or expect range, even when due to a novel or unknown contaminate or cause.

DRAWINGS

For a more complete understanding of the principles disclosed herein, and the advantages thereof, reference is now made to the following descriptions taken in conjunction with the accompanying drawings and exhibits, in which.

Figure 1:
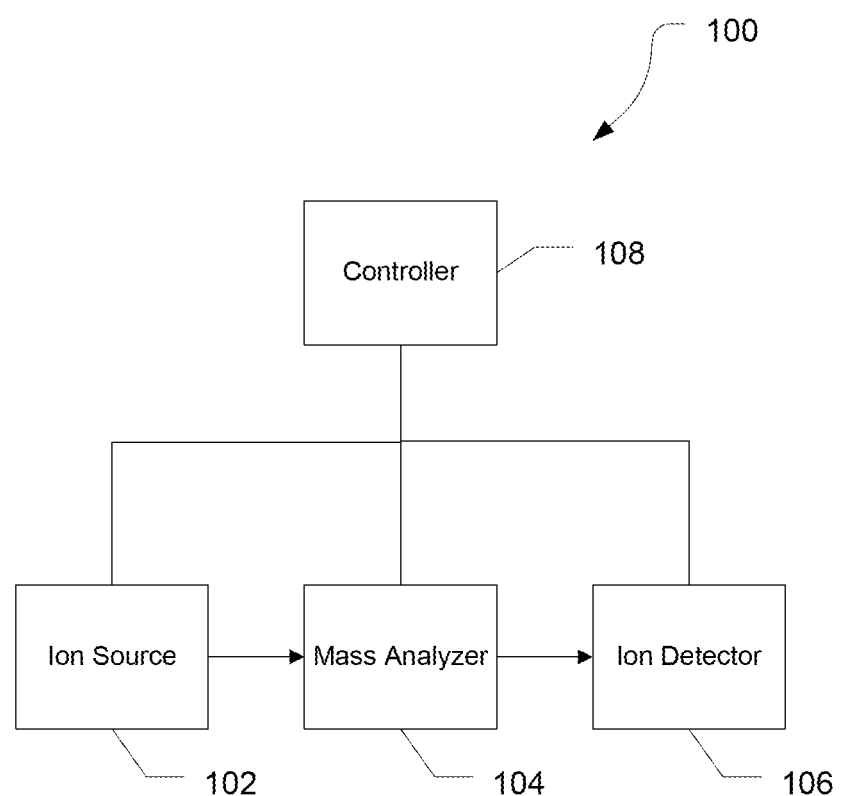
FIG. 1 is a block diagram of an exemplary mass spectrometry system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for ion isolation are described herein and in the accompanying exhibits.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Mass Spectrometry Platforms

Various embodiments of mass spectrometry platform 100 can include components as displayed in the block diagram of FIG. 1. In various embodiments, elements of FIG. 1 can be incorporated into mass spectrometry platform 100. According to various embodiments, mass spectrometer 100 can include an ion source 102, a mass analyzer 104, an ion detector 106, and a controller 108.

In various embodiments, the ion source 102 generates a plurality of ions from a sample. The ion source can include, but is not limited to, a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the mass analyzer 104 can separate ions based on a mass to charge ratio of the ions. For example, the mass analyzer 104 can include a quadrupole mass filter analyzer, a quadrupole ion trap analyzer, a time-of-flight (TOF) analyzer, an electrostatic trap (e.g., ORBITRAP) mass analyzer, Fourier transform ion cyclotron resonance (FT-ICR) mass analyzer, and the like. In various embodiments, the mass analyzer 104 can also be configured to fragment the ions using collision induced dissociation (CID) electron transfer dissociation (ETD), electron capture dissociation (ECD), photo induced dissociation (PID), surface induced dissociation (SID), and the like, and further separate the fragmented ions based on the mass-to-charge ratio.

In various embodiments, the ion detector 106 can detect ions. For example, the ion detector 106 can include an electron multiplier, a Faraday cup, and the like. Ions leaving the mass analyzer can be detected by the ion detector. In various embodiments, the ion detector can be quantitative, such that an accurate count of the ions can be determined.

In various embodiments, the controller 108 can communicate with the ion source 102, the mass analyzer 104, and the ion detector 106. For example, the controller 108 can configure the ion source or enable/disable the ion source. Additionally, the controller 108 can configure the mass analyzer 104 to select a particular mass range to detect. Further, the controller 108 can adjust the sensitivity of the ion detector 106, such as by adjusting the gain. Additionally, the controller 108 can adjust the polarity of the ion detector 106 based on the polarity of the ions being detected. For example, the ion detector 106 can be configured to detect positive ions or be configured to detected negative ions.

Chromatographic Alignment

Figure 2:
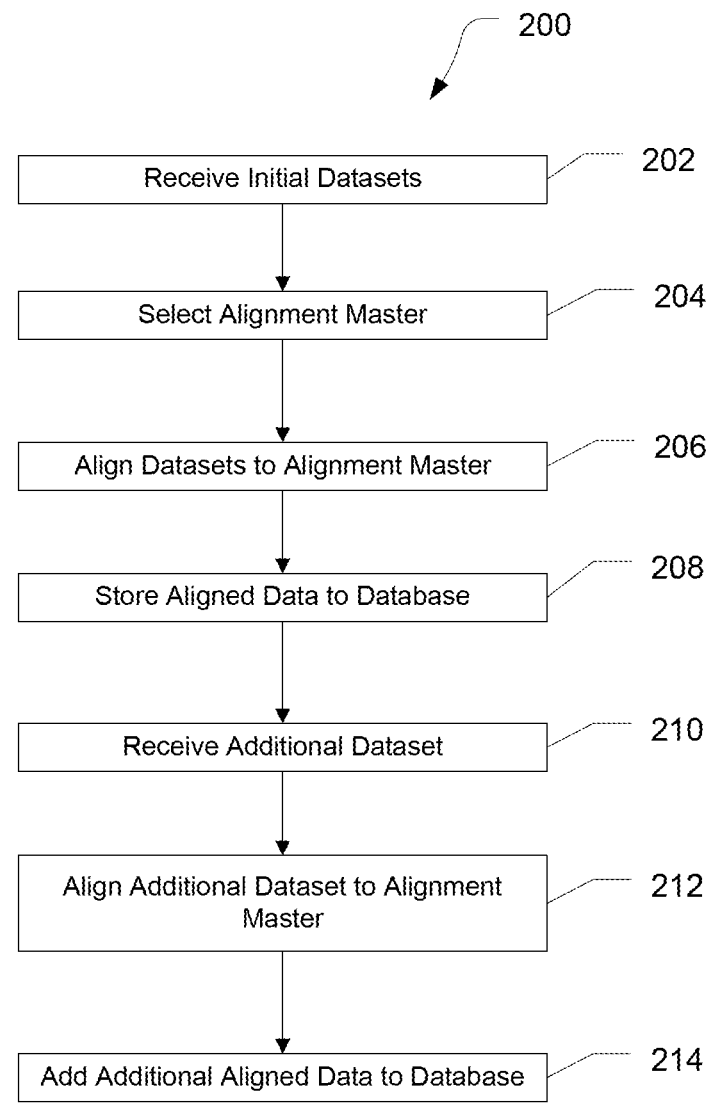
FIGS. 2-4 are flow diagrams illustrating exemplary methods for aligning chromatographic datasets, in accordance with various embodiments.

FIG. 2 is a flow diagram illustrating a method 200 of chromatographic alignment. At 202, the system can receive initial datasets. For example, one or more data acquisition instruments, such as gas chromatography/mass spectrometer (GS/MS) or liquid chromatography/mass spectrometer (LCMS) instruments, can analyze a plurality of samples and provide the resulting datasets to the data analysis system. The initial datasets can include a variety of "normal" samples.

At 204, an alignment master can be selected from the initial datasets. In various embodiments, the dataset with the largest number of features (peaks) can be selected as the alignment master. At 206, each dataset of the initial datasets can be chromatographically aligned to the alignment master. Various techniques are known in the art for chromatographic alignment, such as those disclosed in co-pending U.S. patent application Ser. No. 14/942,864, filed Nov. 16, 2015, incorporated herein in its entirety.

At 208, the aligned data can be stored in a database. In various embodiments, it may not be necessary to store raw data files and the aligned data can be stored as a list of features with their corresponding retention times and intensities.

At 210, additionally datasets can be received. For example, the initial datasets can include a variety of known samples, such as a number of known "normal" samples and the additional datasets can be unknown samples. At 212, the additional samples can be aligned to the alignment master, and the additional aligned data can be stored to the database at 214.

Figure 3:
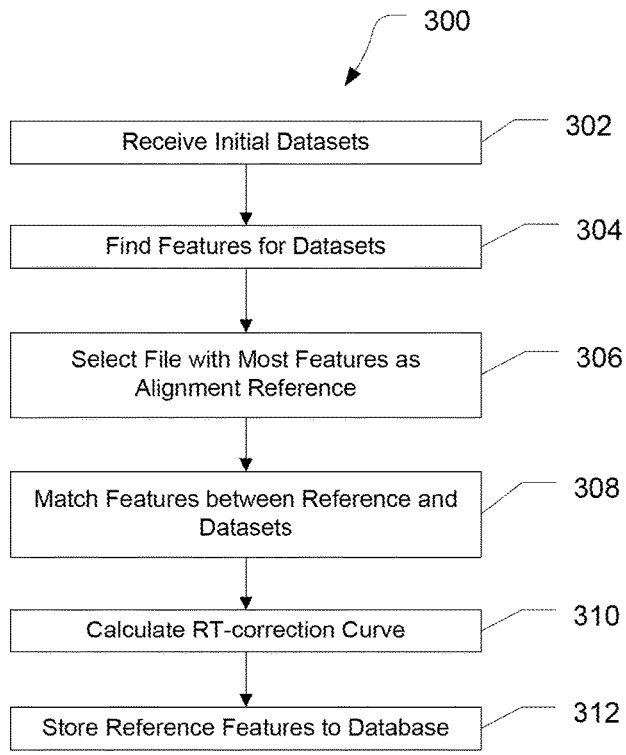

FIG. 3 is a flow diagram illustrating a method 300 of aligning initial datasets. At 302, the system can receive the initial datasets, and at 304, the system can identify a plurality of features within each dataset. For example, the system can detect peaks in the traces of the dataset and group the peaks based on shape and m/z distance. In various embodiments, each dataset can be processed independently to identify the features within the dataset.

At 306, the dataset with the most features can be selected as the alignment reference, and at 308, the system can match features of a dataset with the alignment reference. In various embodiments, the features can be matched by comparing retention time and m/z-values. For each match the retention time difference between the occurrence in the alignment reference and the other dataset is calculated.

At 310, the system can calculate a retention time correction curve for the dataset. For example, utilizing the retention time values of the reference file and the retention time differences determined for the dataset, a support vector regression can be calculated to determine the correction curve.

At 312, the features of the alignment reference can be stored in the database as a profile reference. Additionally, the retention time corrected spectra can be utilized in additional analysis or features of the retention time corrected spectra can be stored in the database. In various embodiments, steps 308, 310, and 312 can be repeated for each dataset of the initial datasets.

Figure 4:
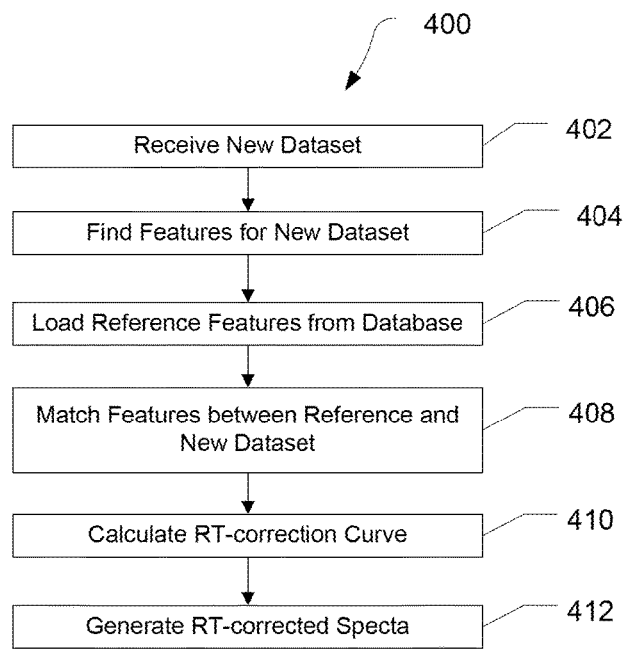

FIG. 4 is a flow diagram illustrating a method 400 of aligning new datasets to the existing datasets, such as a test dataset to a set of known datasets. At 402, the system can receive the new dataset and, at 404, the system can identify features within the new dataset.

At 406, the system can load the reference features from the database, and at 408, the features detected in the new dataset can be compared to the reference features. At 410, the system can calculate a retention time correction curve for the dataset, and at 312, a retention time corrected spectra can be generated. The retention time corrected spectra can be used for further analysis or the features of the retention time corrected spectra can be stored in the database.

Grouping Datasets

Figure 5:
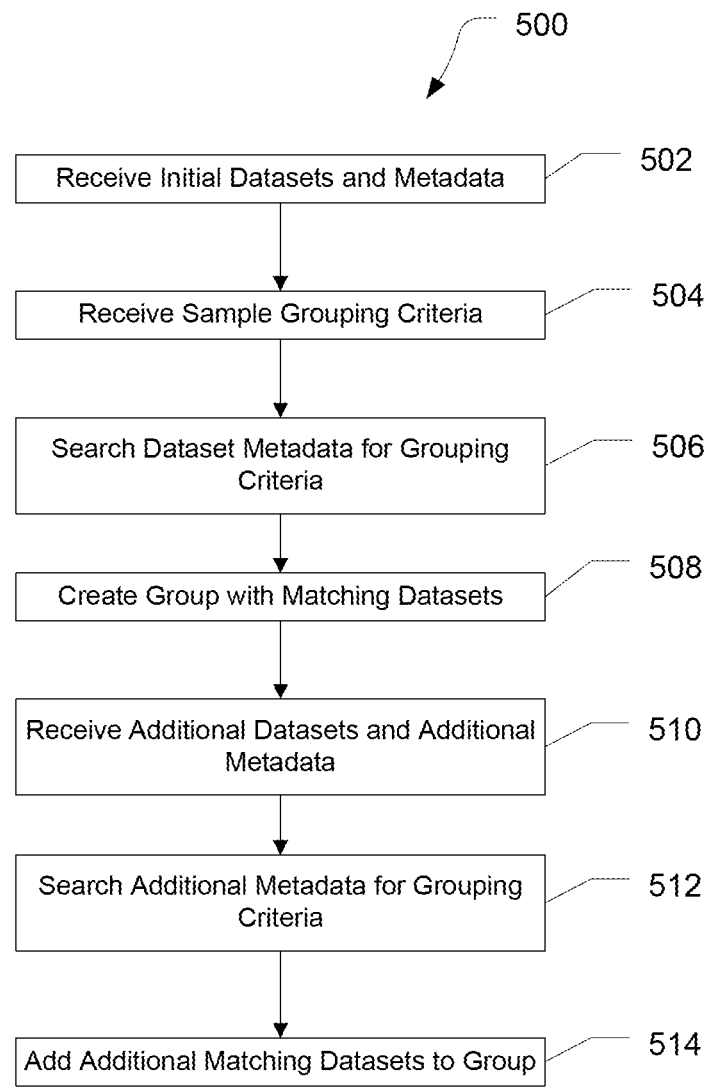
FIG. 5 is a flow diagram illustrating an exemplary method for grouping samples, in accordance with various embodiments.

FIG. 5 is a flow diagram illustrating a method 500 of grouping datasets. In various embodiments, a test sample can be compared to an entire group of reference samples or can be compared to a subgroup. For example, when testing for performance enhancing drug use on race horses, a test sample could be compared to all known good race horse samples or can be compared to race horse samples only from a particular region, of a similar breed, similar age, similar sex, or other criteria that may result in natural but detectable differences between race horse samples.

At 502, the system can receive metadata describing the initial datasets. In various embodiments, the metadata can include region of origin, type of sample, date of sample, species, sex, breed, and the like. For example, metadata of a water sample for environmental testing can indicate where the sample was taken and the date the sample was taken, such as a water sample from a stream in North Dakota can be labeled indicated which stream, the date the sample was taken, geographical information (such as GPS coordinates) and other similar information. In another example, metadata of a food safety sample can indicate the type of food, the origin of the food, and the date the sample was collected, such as a sample of fruit can indicate the country, region, and farm where the fruit was grown, the date of harvest, the location of the processing facility, and the like. In yet another example, metadata of a forensic sample to test for drug use can indicate the sex, age, ethnicity, of the individual, the location of the individual, the time and date the sample was collected, and the like.

At 504, the system can receive a set of grouping criteria, and at 506, the system can search the metadata of the initial datasets for samples matching the grouping criteria. For example, to construct a group of water samples taken from the Mississippi River, the grouping criteria can be the Mississippi River and the system can search the metadata to identify samples where the source is the Mississippi River. At 508, a group can be constructed of all the samples matching the group criteria.

At 510, additional sample metadata can be received, and at 512, the additional metadata can be searched for the grouping criteria. If the additional sample metadata matches the grouping criteria, the additional sample can be added to the group, as indicated at 514.

In various embodiments, the sample can be dynamically grouped by selection criteria such that new samples matching the selection criteria are automatically added to the group. Alternatively, the samples can be statically grouped, such that a specific subset of samples can be selected for the group and adding additional samples to the group requires manually redefining which samples are in the group or the creation of a new group.

Comparing Samples to Reference Set

Figure 6:
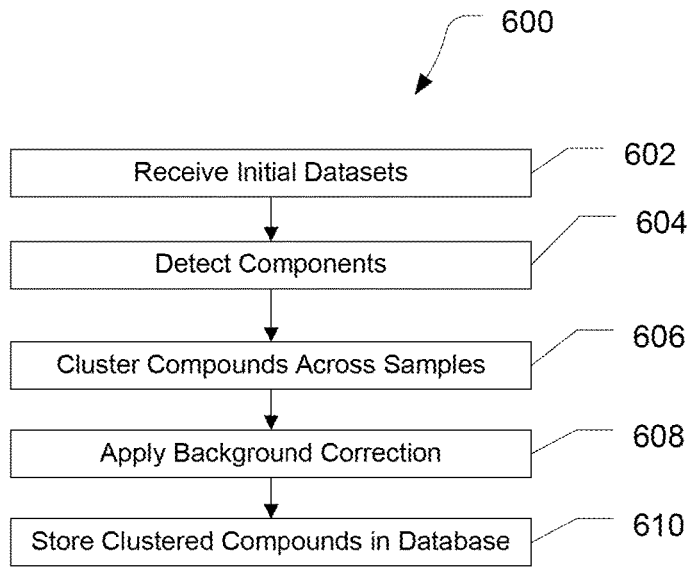
FIGS. 6 and 7 are flow diagrams illustrating exemplary methods for comparing compounds within samples, in accordance with various embodiments.

FIG. 6 is a flow diagram illustrating a method 600 for construction of a reference set. At 602, the system can receive a plurality of initial datasets from known samples, such as the retention time corrected spectra from FIGS. 3 and 4. At 604, components of the samples can be detected. At 606, features can be clustered across samples to identify compounds found in multiple samples. In various embodiments, features common to multiple samples can be identified when the mass-to-charge ratio is within an m/z threshold and the retention time for the feature in the samples falls within a maximum retention time tolerance. Additionally, a second check comparing the retention time difference to the peak width can be performed to determine if the common features are from the same compound.

At 608, background correction can be performed, such as to remove compounds that are from solvents and buffers add during the sample preparation or analysis. In various embodiments, a "blank" dataset can be obtained according to the testing procedure but without the addition of a sample. Compounds in the "blank" dataset can be identified after retention time alignment and the intensities of the "blank" dataset can be recorded. Features in the sample datasets can be discounted if they match the features of the "blank" dataset and have similar intensities. However, if there is a significant change in the intensity as compared to the "blank" dataset, such as at least a 3-fold change in intensity, the compound may not be discounted and can be reported.

At 610, the compounds and the corresponding intensities can be stored in the database.

Figure 7:
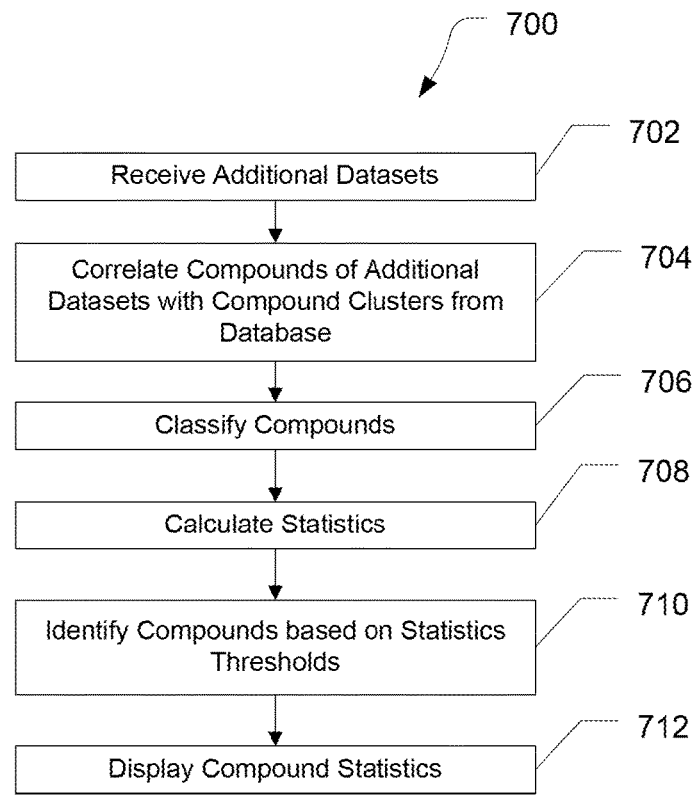

FIG. 7 is a flow diagram illustrating a method 700 for comparison of a sample to a reference set, such as a database of reference samples. At 702, the sample dataset can be received. In various embodiments, a retention time correction can be applied and features of the dataset can be identified.

At 704, compounds of the sample dataset can be correlated with compounds from the reference set. In various embodiments, features of the sample dataset can be matched to compounds in the reference set based on retention time and mass-to-charge ratio. Features of the sample dataset that cannot be matched to the reference set can be identified as additional compounds found in the sample but not in the reference samples. In various embodiments, compounds in the sample dataset and the reference set can be identified as matching (if found in both the sample dataset and the reference set), missing (found in the reference set but not in the sample dataset), and additional (found in the sample dataset but not in the reference set).

In various embodiments, background marking can be performed for compounds identified in the sample. By comparing the intensities of compounds found in the sample dataset to a "blank" dataset, compounds can be marked as matching the "blank" dataset when the intensity is similar to the intensity found in the "blank" dataset, or marked as additional when the intensity is significantly higher than the "blank" dataset.

At 708, statistics can be performed on the compounds, such as by determining the minimum, first quartile, median, third quartile, and maximum for the reference set and comparing the sample dataset to the reference set values. In various embodiments, compounds marked as missing can be provided with an intensity value by missing value imputation, to avoid statistical pitfalls from missing or zero values. In various embodiments, the intensity distribution for a compound in the reference set can be determined and an intensity value can be randomly selected from a lower quantile of the reference set.

At 710, compounds in the sample set that are quantitatively difference from the reference set, such as compounds that are outside of the distribution of the reference set can be identified. Additionally, fold changes and p-values can be calculated for all compounds in the sample set that are outside of the distribution of the reference set.

At 712, the compound statistics can be displayed. In various embodiments, for each compound of the sample dataset, a box plot can be generated of the distribution in the reference set, and data point can be added to represent the intensity value from the sample dataset. The box plot and the data point can be color coded according to the intensity being within, above, or below the range of the reference set. Additionally, for compounds that cross thresholds of significance, the data can be visually marked to highlight significant compounds. The thresholds of significance can include p-values below a selected value, fold change above a selected value, or any combination thereof. In various embodiments, the threshold of significance can be user definable parameters.

In various embodiments, the data storage and analysis can be accomplished by remote data storage nodes and remote compute nodes, such as in the cloud. Datasets (both initial and additional datasets) can be uploaded to the data storage nodes in batches, automatically upon completion data collection for each dataset, or concurrent with the data collection. Furthermore analysis can be performed when a user issues a command or automatically as datasets are received by the data storage nodes.

In various embodiments, it can be desirable for the operator to provide metadata for the sample, configure the data acquisition and analysis, and have the data acquisition system and data analysis system perform data acquisition, data transfer, and data analysis is an automated hands-free manner. For example, an operator can prepare several samples, populate the metadata and configure the acquisition and analysis, load the samples into an auto-sampler, and start the acquisition and analysis process. The data acquisition system can sequentially analyze the samples and the data analysis system can perform the analysis without further user intervention and notify the operator, such as by email, when the data analysis is complete.

Computer-Implemented System

Figure 8:
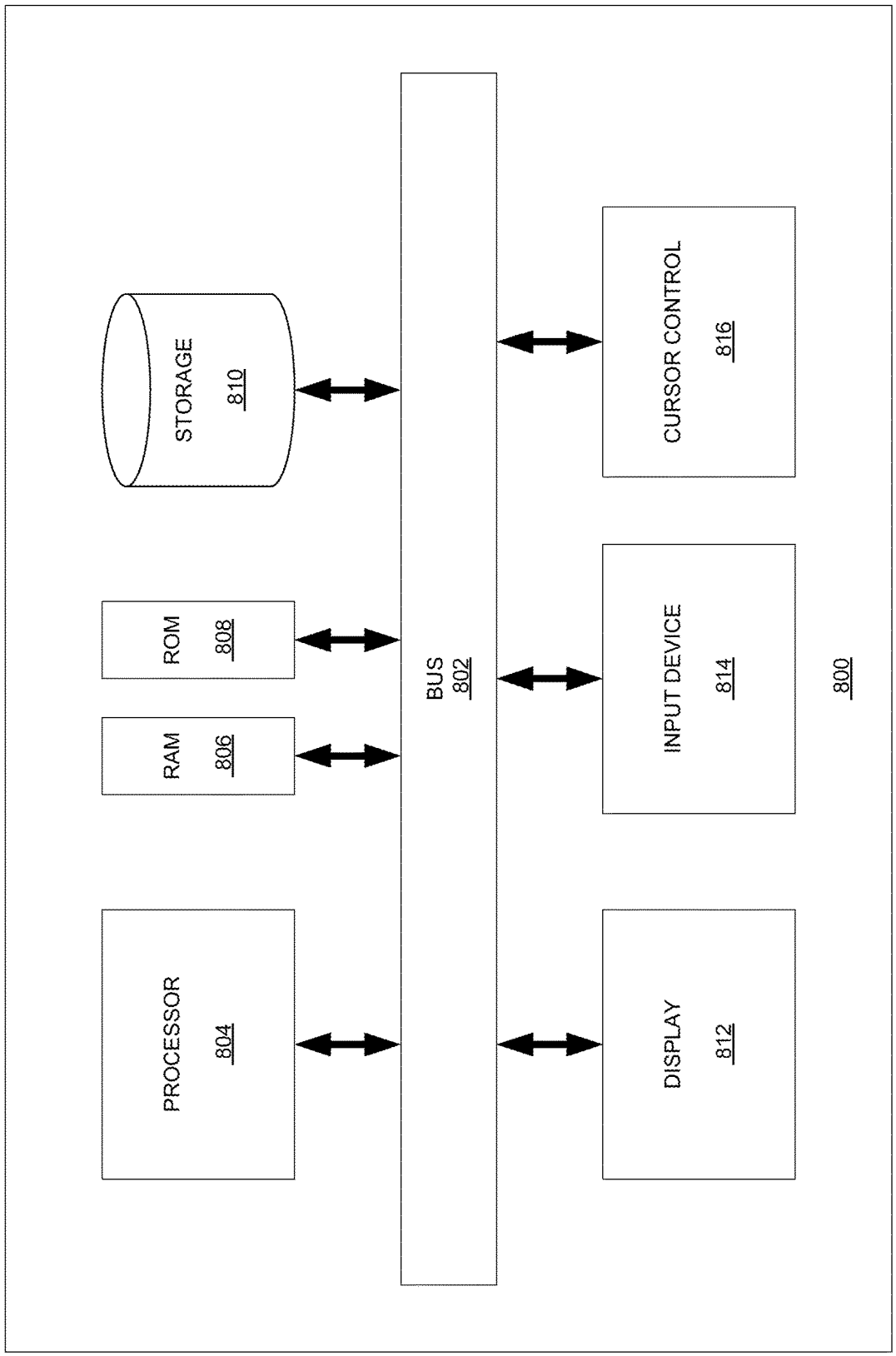
FIG. 8 is a block diagram illustrating an exemplary computer system.

FIG. 8 is a block diagram that illustrates a computer system 800, upon which embodiments of the present teachings may be implemented as which may incorporate or communicate with a system controller, for example controller 108 shown in FIG. 1, such that the operation of components of the associated mass spectrometer may be adjusted in accordance with calculations or determinations made by computer system 800. In various embodiments, computer system 800 can include a bus 802 or other communication mechanism for communicating information, and a processor 804 coupled with bus 802 for processing information. In various embodiments, computer system 800 can also include a memory 806, which can be a random access memory (RAM) or other dynamic storage device, coupled to bus 802, and instructions to be executed by processor 804. Memory 806 also can be used for storing temporary variables or other intermediate information during execution of instructions to be executed by processor 804. In various embodiments, computer system 800 can further include a read only memory (ROM) 808 or other static storage device coupled to bus 802 for storing static information and instructions for processor 804. A storage device 810, such as a magnetic disk or optical disk, can be provided and coupled to bus 802 for storing information and instructions.

In various embodiments, processor 804 can include a plurality of logic gates. The logic gates can include AND gates, OR gates, NOT gates, NAND gates, NOR gates, EXOR gates, EXNOR gates, or any combination thereof. An AND gate can produce a high output only if all the inputs are high. An OR gate can produce a high output if one or more of the inputs are high. A NOT gate can produce an inverted version of the input as an output, such as outputting a high value when the input is low. A NAND (NOT-AND) gate can produce an inverted AND output, such that the output will be high if any of the inputs are low. A NOR (NOT-OR) gate can produce an inverted OR output, such that the NOR gate output is low if any of the inputs are high. An EXOR (Exclusive-OR) gate can produce a high output if either, but not both, inputs are high. An EXNOR (Exclusive-NOR) gate can produce an inverted EXOR output, such that the output is low if either, but not both, inputs are high.

TABLE 1

Logic Gates Truth Table

| INPUTS | | OUTPUTS | | | | | | |
|---|---|---|---|---|---|---|---|---|
| A | B | NOT A | AND | NAND | OR | NOR | EXOR | EXNOR |
| 0 | 0 | 1 | 0 | 1 | 0 | 1 | 0 | 1 |
| 0 | 1 | 1 | 0 | 1 | 1 | 0 | 1 | 0 |
| 1 | 0 | 0 | 0 | 1 | 1 | 0 | 1 | 0 |
| 1 | 1 | 0 | 1 | 0 | 1 | 0 | 0 | 1 |

One of skill in the art would appreciate that the logic gates can be used in various combinations to perform comparisons, arithmetic operations, and the like. Further, one of skill in the art would appreciate how to sequence the use of various combinations of logic gates to perform complex processes, such as the processes described herein.

In an example, a 1-bit binary comparison can be performed using a XNOR gate since the result is high only when the two inputs are the same. A comparison of two multi-bit values can be performed by using multiple XNOR gates to compare each pair of bits, and the combining the output of the XNOR gates using and AND gates, such that the result can be true only when each pair of bits have the same value. If any pair of bits does not have the same value, the result of the corresponding XNOR gate can be low, and the output of the AND gate receiving the low input can be low.

In another example, a 1-bit adder can be implemented using a combination of AND gates and XOR gates. Specifically, the 1-bit adder can receive three inputs, the two bits to be added (A and B) and a carry bit (Cin), and two outputs, the sum (S) and a carry out bit (Cout). The Cin bit can be set to 0 for addition of two one bit values, or can be used to couple multiple 1-bit adders together to add two multi-bit values by receiving the Cout from a lower order adder. In an exemplary embodiment, S can be implemented by applying the A and B inputs to a XOR gate, and then applying the result and Cin to another XOR gate. Cout can be implemented by applying the A and B inputs to an AND gate, the result of the A-B XOR from the SUM and the Cin to another AND, and applying the input of the AND gates to a XOR gate.

TABLE 2

1-bit Adder Truth Table

| INPUTS | | | OUTPUTS | |
|---|---|---|---|---|
| A | B | Cin | S | Cout |
| 0 | 0 | 0 | 0 | 0 |
| 1 | 0 | 0 | 0 | 1 |
| 0 | 1 | 0 | 0 | 1 |
| 1 | 1 | 0 | 1 | 0 |
| 0 | 0 | 1 | 0 | 1 |
| 1 | 0 | 1 | 1 | 0 |
| 0 | 1 | 1 | 1 | 0 |
| 1 | 1 | 1 | 1 | 1 |

In various embodiments, computer system 800 can be coupled via bus 802 to a display 812, such as a cathode ray tube (CRT) or liquid crystal display (LCD), for displaying information to a computer user. An input device 814, including alphanumeric and other keys, can be coupled to bus 802 for communicating information and command selections to processor 804. Another type of user input device is a cursor control 816, such as a mouse, a trackball or cursor direction keys for communicating direction information and command selections to processor 804 and for controlling cursor movement on display 812. This input device typically has two degrees of freedom in two axes, a first axis (i.e., x) and a second axis (i.e., y), that allows the device to specify positions in a plane.

A computer system 800 can perform the present teachings. Consistent with certain implementations of the present teachings, results can be provided by computer system 800 in response to processor 804 executing one or more sequences of one or more instructions contained in memory 806. Such instructions can be read into memory 806 from another computer-readable medium, such as storage device 810. Execution of the sequences of instructions contained in memory 806 can cause processor 804 to perform the processes described herein. In various embodiments, instructions in the memory can sequence the use of various combinations of logic gates available within the processor to perform the processes describe herein. Alternatively hard-wired circuitry can be used in place of or in combination with software instructions to implement the present teachings. In various embodiments, the hard-wired circuitry can include the necessary logic gates, operated in the necessary sequence to perform the processes described herein. Thus implementations of the present teachings are not limited to any specific combination of hardware circuitry and software.

The term "computer-readable medium" as used herein refers to any media that participates in providing instructions to processor 804 for execution. Such a medium can take many forms, including but not limited to, non-volatile media, volatile media, and transmission media. Examples of non-volatile media can include, but are not limited to, optical or magnetic disks, such as storage device 810. Examples of volatile media can include, but are not limited to, dynamic memory, such as memory 806. Examples of transmission media can include, but are not limited to, coaxial cables, copper wire, and fiber optics, including the wires that comprise bus 802.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A system comprising:
a database server; and
a plurality of compute nodes each comprising a processor, the plurality of compute nodes configured to:
receive mass spectrometry data from a plurality of samples;
align the mass spectrometry data to correct for changes in retention time to generate a reference alignment;
cluster features of the mass spectrometry data across the plurality of samples to identify compounds;
store the reference alignment and clustered compound data to the database server;
receive additional mass spectrometry data from additional samples;
align the additional mass spectrometry data to the reference alignment within the database;
correlate the compounds from the additional samples with the clustered compound data;
perform statistical analysis on the compounds from the additional samples to identify compounds meeting threshold criteria; and
provide an indication of the compounds meeting the threshold criteria.

2. The system of claim 1 wherein the mass spectrometry data and the additional mass spectrometry data include liquid chromatography/mass spectrometer data, gas chromatography/mass spectrometer data, or any combination thereof.

3. The system of claim 1 wherein the mass spectrometry data includes a plurality of datasets, and the plurality of compute nodes are further configured to: identify a plurality of features within each dataset, select a first dataset with the most features to be the alignment reference, match features of a second dataset of the plurality of datasets with the alignment reference, and calculate a retention time correction curve for the second dataset.

4. The system of claim 3 wherein the additional mass spectrometry data includes at least one additional dataset, and the plurality of compute nodes are further configured to: identify features within the at least one additional dataset, compare the features detected in the at least one additional dataset with the plurality of features of the mass spectrometry data, and calculate a retention time correction curve for the at least one additional dataset.

5. The system of claim 1 wherein the plurality of compute nodes are further configured to receive metadata describing the mass spectrometry data, receiving a set of group criteria, and constructing a group of datasets of the mass spectrometry data corresponding to the samples matching the group criteria.

6. The system of claim 5 wherein the plurality of compute nodes are further configured to dynamically update the group of datasets when the additional mass spectrometry data is received.

7. The system of claim 1 wherein the plurality of compute nodes are further configured to perform a background correction on the mass spectrometry data and the additional mass spectrometry data to remove compounds that are from solvents and buffers added during sample preparation or analysis.

8. A method comprising:
receiving mass spectrometry data from a plurality of samples;
aligning the mass spectrometry data to correct for changes in retention time to generate a reference alignment;
clustering features of the mass spectrometry data across the plurality of samples to identify compounds;
storing the reference alignment and clustered compound data to the database server;
receiving additional mass spectrometry data from additional samples;
aligning the additional mass spectrometry data to the reference alignment within the database;
correlating the compounds from the additional samples with the clustered compound data;
performing statistical analysis on the compounds from the additional samples to identify compounds meeting threshold criteria; and
providing an indication of the compounds meeting the threshold criteria.

9. The method of claim 8 wherein the mass spectrometry data and the additional mass spectrometry data include liquid chromatography/mass spectrometer data, gas chromatography/mass spectrometer data, or any combination thereof.

10. The method of claim 8 wherein the mass spectrometry data includes a plurality of datasets, and the plurality of compute nodes are further configured to: identify a plurality of features within each dataset, select a first dataset with the most features to be the alignment reference, match features of a second dataset of the plurality of datasets with the alignment reference, and calculate a retention time correction curve for the second dataset.

11. The method of claim 10 wherein the additional mass spectrometry data includes at least one additional dataset, and the plurality of compute nodes are further configured to: identify features within the at least one additional dataset, compare the features detected in the at least one additional dataset with the plurality of features of the mass spectrometry data, and calculate a retention time correction curve for the at least one additional dataset.

12. The method of claim 8 wherein the plurality of compute nodes are further configured to receive metadata describing the mass spectrometry data, receiving a set of group criteria, and constructing a group of datasets corresponding to the samples matching the group criteria.

13. The method of claim 8 further comprising dynamically updating the group of datasets when the additional mass spectrometry data is received.

14. The method of claim 8 wherein the plurality of compute nodes are further configured to perform a background correction on the mass spectrometry data and the additional mass spectrometry data to remove compounds that are from solvents and buffers added during sample preparation or analysis.

15. A method comprising:
uploading a plurality of mass spectrometry datasets from a plurality of samples to a database server; and
initiating a first process on a plurality of compute nodes to:
align the plurality of mass spectrometry datasets to correct for changes in retention time to generate a reference alignment;
cluster features of the mass spectrometry data across the plurality of samples to identify compounds; and
store the reference alignment and clustered compound data to the database server.

16. The method of claim 15 comprising:
uploading at least one additional mass spectrometry datasets from at least one additional samples to the database server; and
initiating a second process on a plurality of compute nodes to:
align the at least one additional mass spectrometry dataset to the reference alignment within the database;
correlate the compounds from the at least one additional samples with the clustered compound data;
perform statistical analysis on the compounds from the additional samples to identify compounds meeting threshold criteria; and
provide an indication of the compounds meeting the threshold criteria.

17. The method of claim 15 wherein the plurality of mass spectrometry datasets and the at least one additional mass spectrometry data include liquid chromatography/mass spectrometer data, gas chromatography/mass spectrometer data, or any combination thereof.

18. The method of claim 15 wherein aligning the plurality of mass spectrometry datasets to correct for changes in retention time to generate a reference alignment further includes:
identifying a plurality of features within each dataset;
select a first dataset with the most features to be the alignment reference;
match features of a second dataset of the plurality of datasets with the alignment reference; and
calculate a retention time correction curve for the second dataset.

19. The method of claim 18 wherein aligning the at least one additional mass spectrometry dataset to a reference alignment within the database further includes:
identifying features within the at least one additional dataset;

comparing the features detected in the at least one additional dataset with the plurality of features of the mass spectrometry data; and calculating a retention time correction curve for the at least one additional dataset.

20. The method of claim 15 further comprising:

uploading metadata describing the plurality of mass spectrometry datasets and a grouping criteria to the database server;

initiating a third process on the plurality of compute nodes initiating to construct a group of datasets corresponding to the samples matching the group criteria.

* * * * *